United States Patent
Hiltebrand et al.

[11] Patent Number: 4,622,151
[45] Date of Patent: Nov. 11, 1986

[54] METHOD AND DEVICE FOR OZONIZATION OF A FLUID

[76] Inventors: Peter Hiltebrand, Blumenau 7, 8184 Bachenbulach; Arthur Ruf, Im Zimikerriet 8, 8603 Schwerzenbach; H. E. Laederach, Kranichweg 30, 3074 Muri; K. Gschwend, En Abbaye, 1891 Verossaz, all of Switzerland

[21] Appl. No.: 682,050
[22] PCT Filed: Mar. 14, 1984
[86] PCT No.: PCT/CH84/00039
§ 371 Date: Nov. 16, 1984
§ 102(e) Date: Jan. 4, 1985
[87] PCT Pub. No.: WO84/03693
PCT Pub. Date: Sep. 27, 1984

[30] Foreign Application Priority Data

Mar. 19, 1983 [CH] Switzerland .................. 1487/83

[51] Int. Cl.$^4$ .................................. C02F 1/78
[52] U.S. Cl. .......................... 210/739; 210/760
[58] Field of Search ............ 210/739, 760, 96.1, 210/143, 192, 199, 205; 422/186.15, 186.2

[56] References Cited

U.S. PATENT DOCUMENTS

| | | | |
|---|---|---|---|
| 3,685,656 | 8/1972 | Schaefer | 210/195 |
| 3,780,163 | 12/1973 | Callighan | 423/210 |
| 4,178,239 | 12/1979 | Lowther | 210/760 X |

FOREIGN PATENT DOCUMENTS

| | | |
|---|---|---|
| 2347826 | 4/1975 | Fed. Rep. of Germany . |
| 2500932 | 7/1975 | Fed. Rep. of Germany . |
| 1159012 | 6/1958 | France . |
| 1591119 | 6/1970 | France . |
| 288176 | 5/1953 | Switzerland . |

*Primary Examiner*—Tom Wyse
*Attorney, Agent, or Firm*—Walter F. Wessendorf, Jr.

[57] ABSTRACT

In order to enhance the operating safety of the ozonizer (1), there is provided between the ozonizer (1) and the mixer (2) a valve (3) operating without any outer energy and in a single flow direction. The mixture is clamped directly to the ozonizer to minimize the self-dissociation of the ozone formed in the ozonizer (1) during the transport to the mixture (2). The disclosed method may be used to sterilize water or gas elements for example evacuation air. It may also be used for the oxidation of chemical elements.

5 Claims, 1 Drawing Figure

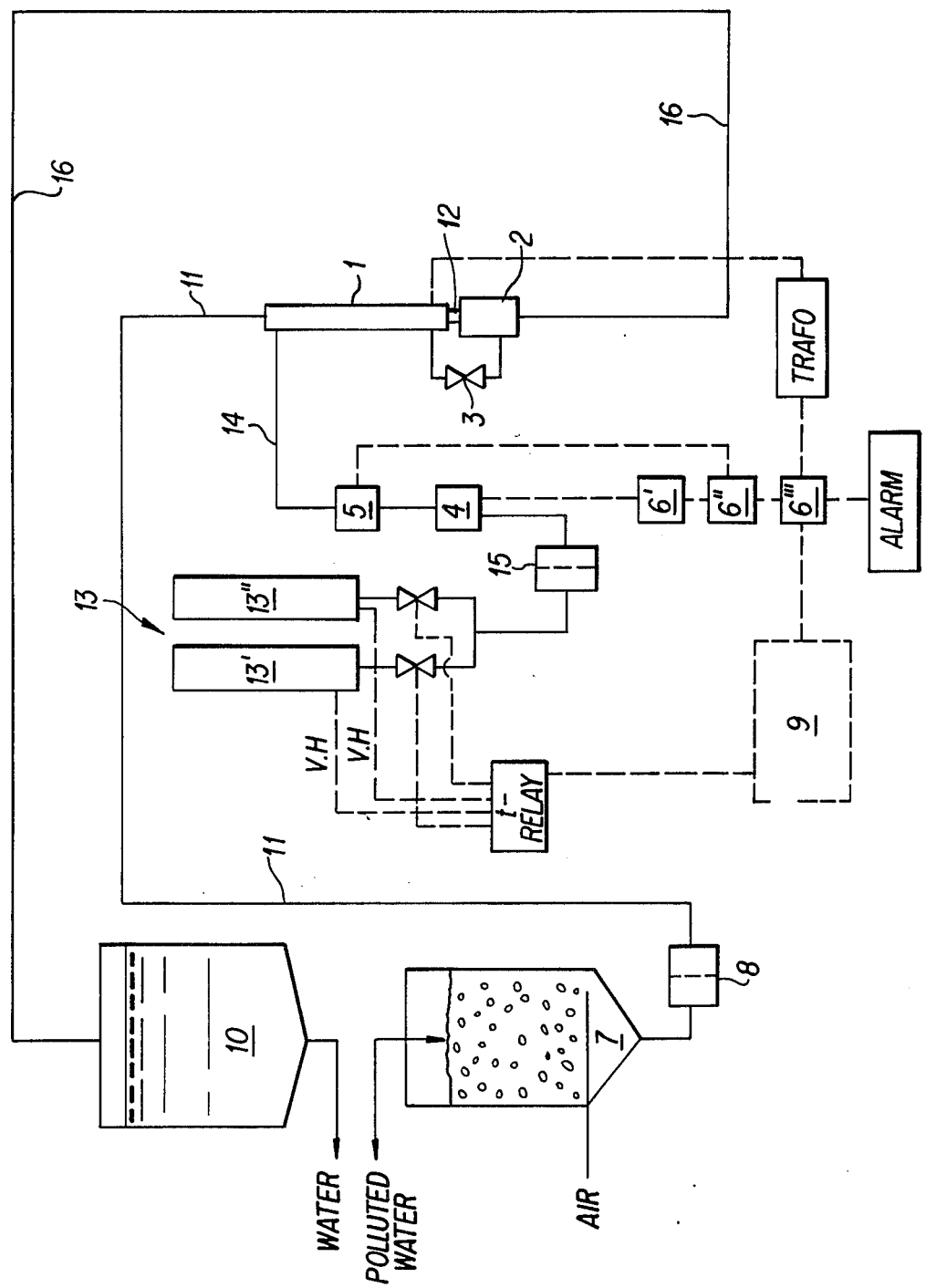

METHOD AND DEVICE FOR OZONIZATION OF A FLUID

Ozone is known as one of the most effective oxidizing agents and it is therefore used for the sterilization of fluids, e.g. drinking water, waste water, mud or exhaust gas, as well as for the non-microbic, i.e. chemical treatment of fluids, e.g. industrial waste water with organic load material.

A great advantage with the use of ozone for carrying out sterilization of fluids is its own decay, i.e. surplus ozone decays into oxygen and prevents a further load on the environment as for example in the case of the sterilization with chlorine. Moreover, no storage is necessary, because ozone can be produced on location from oxygen, e.g. out of air.

The use of ozone for carrying out sterilization of fluids as well as a device for it have been known for a long time. But up to now a reliable operation of the ozonizer has stood in the way of its widespread use.

An analysis has found that for the majority of the cases of damage a return flow of fluid to be brought into contact with the ozone-bearing gas into the ozonizer is responsible: if the fluid is a liquid, a short-circuit current is generated in the ozonizer between the electrodes. If the fluid is a gaseous fluid, a condensation of humidity, i.e. water vapor, on the cooled electrode surfaces causes a change in the electrode gap, so that a local high-energy spark discharge can destroy the ozonizer. The destruction of the ozonizer is carried out identically by solid matter particles deposited on the electrode surface.

An introduction of humidity, or solid matter particles, respectively, into the ozonizer is eliminated to a large extent according to the state of the art by gas driers and dust filters. These safety measures are insufficient when the ozonizer is of the spark discharge type and is cooled by the fluid to be treated. When the fluid is cold, the relative humidity of the air, even after passing a drier may be too high, so that condensation of water occurs in the spark discharge area which may destroy the ozonizer. It is therefore the object of the invention to disclose a method and an implementation of the method that do not suffer from the described drawbacks.

By using a valve that operates without the requirement of foreign energy and only allows one direction of flow, preferably a nonreturn valve equipped with a membrane, an intrusion of fluid into the ozonizer is also prevented when the ozone equipment is turned off, i.e. the protection is also ensured in the case of a power failure. A mixer arranged on the ozonizer minimizes the ozone transportation time between the ozonizer and the mixer. Due to the minimal transportation time the natural ozone decay is minimized, so that a maximum of the ozone produced in the ozonizer is admixed to the fluid and can become effective with it.

Further development of the invention increases the operational safety of the method by using a measuring device for monitoring the relative humidity determines a too high humidity content of the gas and thereby interrupts the ozonizer current. In this way a condensation of water on the cooled electrodes is prevented. Moreover, by using dry gas the ozone yield is increased and the formation of nitrous gases is minimized.

Monitoring of the gas throughput ensures a continuous feeding of the ozonizer with fresh gas and thus a continuous production of ozone. If the gas throughput falls below a preferably adjustable nominal value, in this case also the ozonizer current is interrupted.

In the preferred use of a measurement device for determining the relative humidity as well as a gas throughput meter the error reporting signals are practically correlated by an "OR-connection". The resulting signal of this connection can e.g. be used to drive an alarm device (acoustically and/or optically) and/or to drive further elements, e.g. the fluid pump or the water vapor removal device.

Of course the error reporting signal of each individual measurement device can also be processed further separately.

In an embodiment of the method the gas to be ozonized is conducted before its entry into the ozonizer through a water vapor removal device, e.g. a dryer filled with silica gel with two columns.

So that no solid material particles, by which e.g. dust from the surroundings or wear material from the drier can be understood, intrude into the ozonizer or the measurement device(s), a filter is practically installed into the connecting line for the gas to be ozonized between the drier and the ozonizer.

In a further embodiment of the method, the fluid is preventilated ozone-free with a gas containing oxygen before its entry into the mixer where it comes into contact with the ozone-bearing gas. This preventilation serves to activate e.g. microorganisms present in the form of spores in the fluid, whose breathing system begins to work in this way. Only if the breathing system is activated can the ozone carry out its sterilizing effect.

So that the microorganisms killed off cannot serve as new nutrient medium for eventually not killed off microorganisms, in a further embodiment of the method, the fluid is filtered after coming into contact with the ozone containing gas. The filtered fluid is then fed to a further mixer in which an additional dosing of ozone is effected. Because the fluid flowing out of the filter is to a large extent free of active microorganisms capable of division or dead cellular material the ozone dosed in the further mixer serves mostly to build up a sterilizing ozone buffer in the fluid. In this way it can be prevented that the ozone treated fluid which is preferably stored in a storage container is subjected to a new attack by microorganisms, or that microorganisms still in active condition eventually passing through the filter begin to propagate. So that the filter is not loaded with additional microorganisms in case of required cleaning it is practical to flush back the filter with already ozonized fluid.

A preferred embodiment of the device is equipped with a main independent power supply. It can be a generator with a lined up internal combustion engine. An accordingly equipped device can serve e.g. as a mobile drinking water treatment device among other things in remote areas or in cases of disasters.

Apart from the treatment of drinking water, a treatment, i.e. sterilization of waste water or flow-capable mud or rediluted mud e.g. from sewage-treatment plants is possible with the method according to the invention.

Further all oxidizable substances can be oxidized which is especially important for the removal or transformation of bad-smelling materials or materials impairing taste.

In the following, the invention is explained with reference to an application example.

The sole FIGURE shows a block-diagram of a device used to treat brackish water polluted by liquid manure. The device comprises a power supply 9 that operates independent of the mains, which supplies power both to a transformer indicated as "Trafo" and to the relay marked "t-Relay".

A tube-shaped ozonizer 1 is vertically mounted in a water conduit 11. In this way the water cools the ozonizer. A venturi mixer 2 is flange-connected with the ozonizer immediately via a PVC coupling piece 12. The water flowing through the venturi mixer sucks air to be ozonized under the influence of the underpressure building up within the mixer through the silica gel filled drier 13, conduit 14 and the ozonizer 1, in which part of the air oxygen is transformed into ozone according to the known reaction equilibrium. The ozone bearing gas leaves the ozonizer 1 via a conduit containing the membrane equipped nonreturn valve 3 which works without requiring foreign power supply, into the mixer 2.

In the highly turbulent contact zone of the mixer the ozone bearing gas is is dispersed as fine bubbles into the water. Thereby a large specific gasliquid contact area is created and thus an optimal ozone transfer into the water achieved.

In the connecting conduit 14 between drier 13 and ozonizer 1 an air throughput meter 5 and a measurement device 4 for determination of the relative humidity are each installed. These serve to monitor the operating conditions in the ozonizer as is explained in the following.

Ambient air is sucked into one 13' or two columns 13,',13" of the drier due to the underpressure created in the venturi mixer. The silica gel present in the drier column removes the water vapor content from the air. To control this drying process the humidity meter 4 continuously measures the relative humidity of the air flowing out of the drier. If this humidity rises above a manually adjustable nominal value, the electronic comparing unit 6' following the humidity meter emits a signal. The magnitude of this nominal value depends on the application and is especially influenced by the temperature of the coldest part of the ozonizer. It is very important that the temperature does not reach or fall below the condensation point at this point of the air to be ozonized. Because the ozonizer is water-cooled, i.e. through the brackish water to be sterilized, the temperature can be approximately used to determine the nominal value for the comparing unit 6'.

It is also possible to use the output signal of the comparing unit 6' for redirecting the air flow over the two columns 13', 13" and at the same time starting a thermal regeneration process in the column 13' used up to now. But because a air throughput meter 5 is used apart from the humidity meter 4 for monitoring the air throughput through the ozonizer, the said signal is logically combined with the signal of the humidity meter by an "or-connection unit" 6". The redirection of the dryer columns is solely effected by timing relay marked Relay in the drawing. When the timing relay is activated it closes the valve connecting for example drier column 13' to conduit 14 and switches on heating line V, H to that drier. At the same time it opens the valve connecting drier column 13 to conduit 14. The air throughput meter is designed as a flow meter. A photoelectric device or a proximity switch senses the position of the float body. If this falls under an adjustable nominal value the air throughput meter emits a signal. The nominal value of the air throughput meter is determined by the requirement for ozone which corresponds to a certain air throughput.

The output signal of the "or member" 6" thus controls a relay 6''', when the air humidity nominal value is exceeded as well as when the humidity drops below it, which interrupts the ozonizer current and activates an alarm unit (horn, siren, or blinking light) at the same time. Because silica gel dust can form in the dryer if it is operated over a longer period of time, or dust can intrude from the environment through the dryer into the connecting conduit 14 to the ozonizer, a fine dust filter 15 is installed in direction of air flow in front of the measurement devices.

The mixture of water and ozone-bearing gas leaving the mixer 2 is guided through a tube conduit 16, the length of which is determined by the desired contact time of the two phases, into a collection container 10. In this tube conduit static mixing elements can be additionally installed. But it is also possible to install a phase-dividing element, e.g. a gas separator, in front of the collection container. The gas separator is preferred in particular for swimming pool water sterilization installations, so that no gaseous ozonze layer which would endanger the health of the swimmers could form over the swimming pool that has taken over the function of the collection tank in this case.

Because sporelike, i.e. not actively breathing microorganisms are often present in brackish waters, and these can not be destroyed in the stated form by ozone, in a further development of the invention a ventilation device 7, for example in the form of a ventilation tank or a bubble column is added in front of the ozonizer. Due to the introduced oxygen the spore-like organisms are activated and can then be destroyed by the subsequent contact with ozone.

One or several filters such as filter 8, e.g. active coal filters or sand filters, in front of or after the mixer clean the fluid from solid materials, or absorb its remaining ozone content, respectively. These filters are preferably flushed back sterilely with already ozonized fluid.

Because the fluid to be treated with ozone can also be gaseous, e.g. exhaust air, a gas-mixing element, e.g. a static mixer or also only a T-element is preferably installed instead of the venturi mixer. Because such elements are usually not self-suctioning, a gas pumping organ must be additionally provided for the transportation of the gas to be ozonized in the ozonizer.

If large amounts of fluid are to be sterilized or oxidized, the fluid flow can be distributed onto several ozonizers working in parallel. The air treated by the drier can be conducted over a single humidity or gas throughput meter each, respectively, or over one of these meters each per ozonizer. It is decisive that a non-return valve is provided between each ozonizer and mixer and that the mixers are directly flange-connected with the corresponding ozonizers. It is also possible to use a multiple mixer with individual flange-connected ozonizers.

We claim:

1. In an ozonizer having gapped electrodes for producing an ozone-bearing gas for treating a fluid, wherein said ozone-bearing gas is produced from an input gas into said ozonizer by means of electrical spark discharge between said electrodes, and wherein said ozonizer is cooled by the fluid to be treated: the method of monitoring the relative humidity and gas throughput of the input gas before its entry into the ozonizer, interrupting the operating current to the electrodes to prevent destruction of the ozonizer when the relative humidity of the input gas exceeds a nominal value beyond which water condensation occurs on the electrode surfaces narrowing the electrode gap with resulting local high-energy spark discharge or short-circuiting of the electrodes; and interrupting the operating current to the electrodes when throughput of the input gas is less than the requirement for the production of such ozone-bearing gas.

2. The method of claim 1 wherein an error operating signal is produced when the operating current to the electrodes is interrupted to prevent destruction of the ozonizer when the relative humidity of the input gas exceeds such nominal value beyong which water condensation occurs on the electrode surfaces and wherein an error operating signal is produced when the operating current to the electrodes is interrupted when throughput of the input gas is less than the requirement for the production of such ozone-bearing gas.

3. The method of claim 1 wherein the input gas is dried and filtered before it enters the ozonizer, wherein the ozone-bearing gas produced in the ozonizer flows out of the ozonizer through a one-way flow valve means, and wherein the ozone-bearing gas flowing through the one-way flow valve means is thereafter mixed with the fluid.

4. The method of claim 1 wherein the fluid is brought into contact with oxygen or an oxygen-enriched gas before it is treated by the ozone-bearing gas.

5. The method of claim 4 wherein solid particles are filtered out of the fluid before it is treated by the ozone-bearing gas.

* * * * *